(12) United States Patent
Hauck

(10) Patent No.: US 10,687,725 B2
(45) Date of Patent: *Jun. 23, 2020

(54) NAVIGATIONAL REFERENCE DISLODGEMENT DETECTION METHOD AND SYSTEM

(71) Applicant: St. Jude Medical, Atrial Fibrillation Division, Inc., St. Paul, MN (US)

(72) Inventor: John A. Hauck, Shoreview, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1251 days.

This patent is subject to a terminal disclaimer.

(21) Appl. No.: 14/946,864

(22) Filed: Nov. 20, 2015

(65) Prior Publication Data

US 2016/0331268 A1 Nov. 17, 2016

Related U.S. Application Data

(63) Continuation of application No. 11/647,277, filed on Dec. 29, 2006, now Pat. No. 9,220,439.

(51) Int. Cl.
*A61B 5/00* (2006.01)
*A61B 5/042* (2006.01)
(Continued)

(52) U.S. Cl.
CPC ............... *A61B 5/042* (2013.01); *A61B 5/06* (2013.01); *A61B 5/063* (2013.01); *A61B 5/7221* (2013.01);
(Continued)

(58) Field of Classification Search
CPC .............................. A61B 5/042; A61B 5/7221
See application file for complete search history.

(56) References Cited

U.S. PATENT DOCUMENTS

| 5,263,493 A | 11/1993 | Avitall |
| 5,280,429 A | 1/1994 | Withers |

(Continued)

FOREIGN PATENT DOCUMENTS

WO 2008/083111 7/2008

OTHER PUBLICATIONS

Estner, Heidi Luise, "Electrical isolation of pulmonary veins in patients with atrial fibrillation: reduction of fluoroscopy exposure and procedure duration by the use of a non-fluoroscopic navigation system (NavX®)", Europace, vol. 8, pp. 583-587, Jul. 10, 2006.

(Continued)

*Primary Examiner* — Rochelle D Turchen
(74) *Attorney, Agent, or Firm* — Wiley Rein LLP

(57) ABSTRACT

A method of tracking a position of a catheter within a patient includes securing a navigational reference at a reference location within the patient, defining the reference location as the origin of a coordinate system, determining a location of an electrode moving within the patient relative to that coordinate system, monitoring for a dislodgement of the navigational reference from the initial reference location, for example by measuring the navigational reference relative to a far field reference outside the patient's body, and generating a signal indicating that the navigational reference has dislodged from the reference location. Upon dislodgement, a user may be provided with guidance to help reposition and secure the navigational reference to the initial reference location, or the navigational reference may be automatically repositioned and secured to the initial reference location. Alternatively, a reference adjustment may be calculated to compensate for the changed reference point/origin.

7 Claims, 2 Drawing Sheets

(51) Int. Cl.
*A61B 34/20* (2016.01)
*A61B 5/06* (2006.01)

(52) U.S. Cl.
CPC ...... *A61B 34/20* (2016.02); *A61B 2034/2051* (2016.02); *A61B 2034/2053* (2016.02); *A61B 2034/2072* (2016.02)

(56) References Cited

U.S. PATENT DOCUMENTS

| | | |
|---|---|---|
| 5,335,668 A | 8/1994 | Nardella |
| 5,487,385 A | 1/1996 | Avitall |
| 5,500,011 A | 3/1996 | Desai |
| 5,568,809 A | 10/1996 | Ben-Haim |
| 5,694,945 A | 12/1997 | Ben-Haim |
| 5,697,377 A | 12/1997 | Wittkampf |
| 5,840,025 A | 11/1998 | Ben-Haim |
| 5,842,984 A | 12/1998 | Avitall |
| 5,954,665 A | 9/1999 | Ben-Haim |
| 5,983,126 A | 11/1999 | Wittkampf |
| 6,115,626 A | 9/2000 | Whayne et al. |
| 6,129,669 A | 10/2000 | Panescu et al. |
| 6,226,542 B1 | 5/2001 | Reisfeld |
| 6,233,477 B1 | 5/2001 | Chia et al. |
| 6,332,089 B1 | 12/2001 | Acker |
| 6,640,119 B1 | 10/2003 | Budd et al. |
| 6,728,562 B1 | 4/2004 | Budd et al. |
| 6,858,003 B2 | 2/2005 | Evans et al. |
| 6,939,309 B1 | 9/2005 | Beatty et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 2004/0254437 A1 | 12/2004 | Hauck |
| 2005/0119639 A1 | 6/2005 | McCombs et al. |
| 2005/0203382 A1 | 9/2005 | Govari et al. |
| 2005/0222554 A1 | 10/2005 | Wallace et al. |
| 2006/0084863 A1 | 4/2006 | Kluzik et al. |
| 2006/0090502 A1 | 5/2006 | Moll et al. |
| 2006/0100610 A1 | 5/2006 | Wallace et al. |
| 2007/0060833 A1 | 3/2007 | Hauck |
| 2007/0185486 A1 | 8/2007 | Hauck et al. |
| 2007/0255327 A1* | 11/2007 | Cho ............... A61N 1/3622 607/18 |
| 2008/0009758 A1 | 1/2008 | Voth |

OTHER PUBLICATIONS

Krum, David, "Catheter Location, Tracking, Cardiac Chamber Geometry Creation, and Ablation Using Cutaneous Patches", Journal of Interventional Cardiac Electrophysiology, No. 12, pp. 17-22, Jan. 1, 2005.

* cited by examiner

NAVIGATIONAL REFERENCE DISLODGEMENT DETECTION METHOD AND SYSTEM

CROSS-REFERENCE TO RELATED APPLICATIONS

This application is a continuation of U.S. application Ser. No. 11/647,277, filed 29Dec. 2006, now pending, which is hereby incorporated by reference as though fully set forth herein.

BACKGROUND OF THE INVENTION a. Field of the Invention

The instant invention relates generally to the navigation of a medical device through a patient. More specifically, the instant invention relates to a method and system for detecting and controlling for the movement of a reference point utilized in a localization system employed in navigating a medical device through a patient, and in particular through the heart and vasculature of the patient.

b. Background Art

It is well known to generate heart chamber geometry in preparation for cardiac diagnostic or therapeutic procedures. Often, a mapping catheter tip is placed against the wall of the heart chamber and the three-dimensional coordinates of the mapping catheter tip measured using a localization system. The three-dimensional coordinates become a geometry point. Multiple measurements are taken as the mapping catheter is moved within the heart chamber, resulting in a cloud of geometry points (also referred to as "location data points") that defines the geometry of the heart chamber. Various surface construction algorithms may then be applied to wrap a surface around the cloud of geometry points to obtain a representation of the heart chamber geometry.

It is desirable for the three-dimensional coordinate system to have a stable reference point or origin. While any stable position will suffice, it is desirable for many reasons to utilize a reference point that is proximate to the mapping catheter. Thus, a catheter-mounted reference electrode is often inserted into the heart and positioned in a fixed location, for example the coronary sinus, to establish the origin of the coordinate system relative to which the location of the mapping catheter will be measured.

It is known, however, that the stationary reference electrode may become dislodged. For example, the mapping catheter may collide or become entangled with the reference electrode, or the physician moving the mapping catheter may inadvertently jostle the catheter carrying the reference electrode. The reference electrode may also be dislodged by patient movement.

When the reference electrode becomes dislodged, it effectively shifts the origin of the coordinate system relative to which the position of the mapping catheter is measured. Unless the dislodgement is detected and accounted for, positions of the mapping catheter measured after the dislodgement will be invalid.

BRIEF SUMMARY OF THE INVENTION

It is therefore desirable to be able to detect dislodgement of the electrode or other navigational reference that defines the origin of the coordinate system relative to which body geometries are measured.

It is also desirable to guide a user in reestablishing the original position of the navigational reference.

It is further desirable to provide a method by which the original position of the navigational reference may be reestablished.

In addition, it is desirable to provide a method that accounts for the dislodged location of the navigational reference without requiring reestablishment of the original position of the navigational reference.

Disclosed herein is a method of tracking a position of a catheter within a patient's body. The method includes the steps of: securing a navigational reference at an initial reference location within a patient's body; defining the initial reference location as a reference point for a coordinate system for locating positions of points in space; providing a moving electrode within the patient's body; determining a location of the moving electrode and providing location information data for the moving electrode, the location information data comprising position information that defines the location of the moving electrode in the coordinate system that uses the initial reference location as its reference point; monitoring for a dislodgement of the navigational reference from the initial reference location; and generating a signal indicating that the navigational reference has dislodged from the initial reference location.

A user may be provided with guidance to help reposition and secure the navigational reference to the initial reference location. Alternatively, a computer may be used to control a servo-controlled catheter to reposition and secure the navigational reference to the initial reference location. In still other embodiments of the invention, a location of the navigational reference is determined after it has dislodged from the reference location, and a reference adjustment is calculated to compensate for the navigational reference having changed positions. The reference adjustment may then be used to generate location information data for the moving electrode with reference to the coordinate system that uses the initial reference location as its reference point.

Dislodgement may be detected by monitoring an output signal from the navigational reference for a value in excess of a threshold. For example, the velocity of the navigational reference may be monitored for a velocity in excess of a preset dislodgement threshold. In some embodiments of the invention, a far field reference is provided outside the patient's body, and both the navigational reference and the far field reference are coupled to a circuit to generate an output signal that is monitored for a signal indicative of dislodgement, for example a signal with an absolute amplitude above a dislodgment threshold. The output signal is preferably filtered with both a high pass and a low pass filter, and will typically be a signal indicative of the location of the navigational reference relative to the far field reference. The low pass filter preferably has a cutoff frequency of 0.1 Hz, while the high pass filter preferably has a cutoff frequency of about 0.001 Hz. It is understood that the filtering may be accomplished by filtering analog signal, or the filtering process may also be accomplished using digital signal processing algorithms that operate on a digital signal, which may be generated using analog-to-digital converters as is well known in the art.

Optionally, the moving electrode and the navigational reference include respective first and second measurement electrodes to measure electrophysiology information, and the output of the first measurement electrode may be adjusted by compensating for at least one signal that is common to each of the first and second measurement electrodes when electrophysiology measurements are taken simultaneously with the first and second measurement electrodes.

Also disclosed is a method of measuring electrophysiology information using multiple electrodes that includes the steps of: providing a localization system that determines locations of objects within a three-dimensional space and generates location information data comprising position information determined relative to at least one reference; securing a local reference at an internal reference location within a patient's body, the local reference comprising a first measurement electrode; providing a far field reference outside the patient's body at an external reference location; providing a second measurement electrode within the patient's body; using the localization system to determine a location of the second measurement electrode and providing location information data for the second measurement electrode comprising position information determined relative to the internal reference location as a reference point; simultaneously taking electrophysiology measurements using each of the first and second measurement electrodes and adjusting the output of the second measurement electrode by compensating for at least one signal that is common to each of the first and second measurement electrodes; monitoring for a dislodgement of the local reference from the internal reference location; and generating a signal indicating that the local reference has dislodged from the internal reference location. Optionally, the method also includes: determining a dislodged location of the local reference after it has dislodged from the internal reference location; and calculating an adjustment to compensate for a change in locations between the internal reference location and the dislodged location. Position information for the second measurement electrode may then be determined relative to the internal reference location as a reference point by applying the adjustment to a location of the second measurement electrode relative to the local reference in the dislodged location.

According to another embodiment of the invention, a system for measuring electrophysiology information using multiple electrodes includes: a localization system that determines locations of objects within a three-dimensional space and that generates location information data comprising position information determined relative to at least one reference; a local reference that can be secured at an internal reference location within a patient's body, the local reference comprising a first measurement electrode that generates a first measurement signal; a far field reference that can be secured at an external reference location outside the patient's body; a second measurement electrode that can be placed within the patient's body, the second measurement electrode generating a second measurement signal; a common mode processor to take electrophysiology measurements using each of the first and second measurement electrodes and to adjust the output of the second measurement electrode by removing at least one signal component that is common to each of the first and second measurement signals; an output processor coupled to the localization system that determines a location of the second measurement electrode and provides location information data for the second measurement electrode, the location information data comprising position information determined relative to the internal reference location as a reference point; and a controller that monitors for dislodgement of the local reference from the internal reference location and that generates a signal indicating that the local reference has dislodged from the internal reference location. Optionally, the system may further include one or more of the following: a servo mechanism to reposition and secure the local reference to the internal reference location; an adjustment processor to determine a dislodged location of the local reference and to calculate a reference adjustment that compensates for the local reference having moved from the internal reference location to the dislodged location; and a filtering processor, including a high pass filter and a low pass filter, that outputs a filtered signal, which the controller monitors for an indication of dislodgement of the local reference from the internal reference location.

A technical advantage of the present invention is that it may be used to alert a user to dislodgement of the navigational reference.

Another advantage of the present invention is that it may guide the user in correcting the dislodgement.

Yet another advantage of the present invention is that it can automatically correct for the dislodgment, for example by automatically reestablishing the navigational reference in its original position, or, alternatively, by calculating a reference adjustment to compensate for the changed position of the navigational reference.

The foregoing and other aspects, features, details, utilities, and advantages of the present invention will be apparent from reading the following description and claims, and from reviewing the accompanying drawings.

DETAILED DESCRIPTION OF THE INVENTION

The present invention, which is preferably practiced in connection with a localization system, automatically detects dislodgement of a navigational reference for the localization system. In addition, the present invention provides methods of automatically correcting for the dislodgment or to guide a user, e.g., a physician, in repositioning the navigational reference at its original location. For illustrative purposes, the present invention will be described in the context of a cardiac diagnostic or therapeutic procedure, such as an electrophysiology study. One of ordinary skill in the art will appreciate, however, that the invention may be practiced with equal success in any number of other applications, and, accordingly, the illustrative embodiment used herein to describe the invention should not be regarded as limiting.

Figure 1:
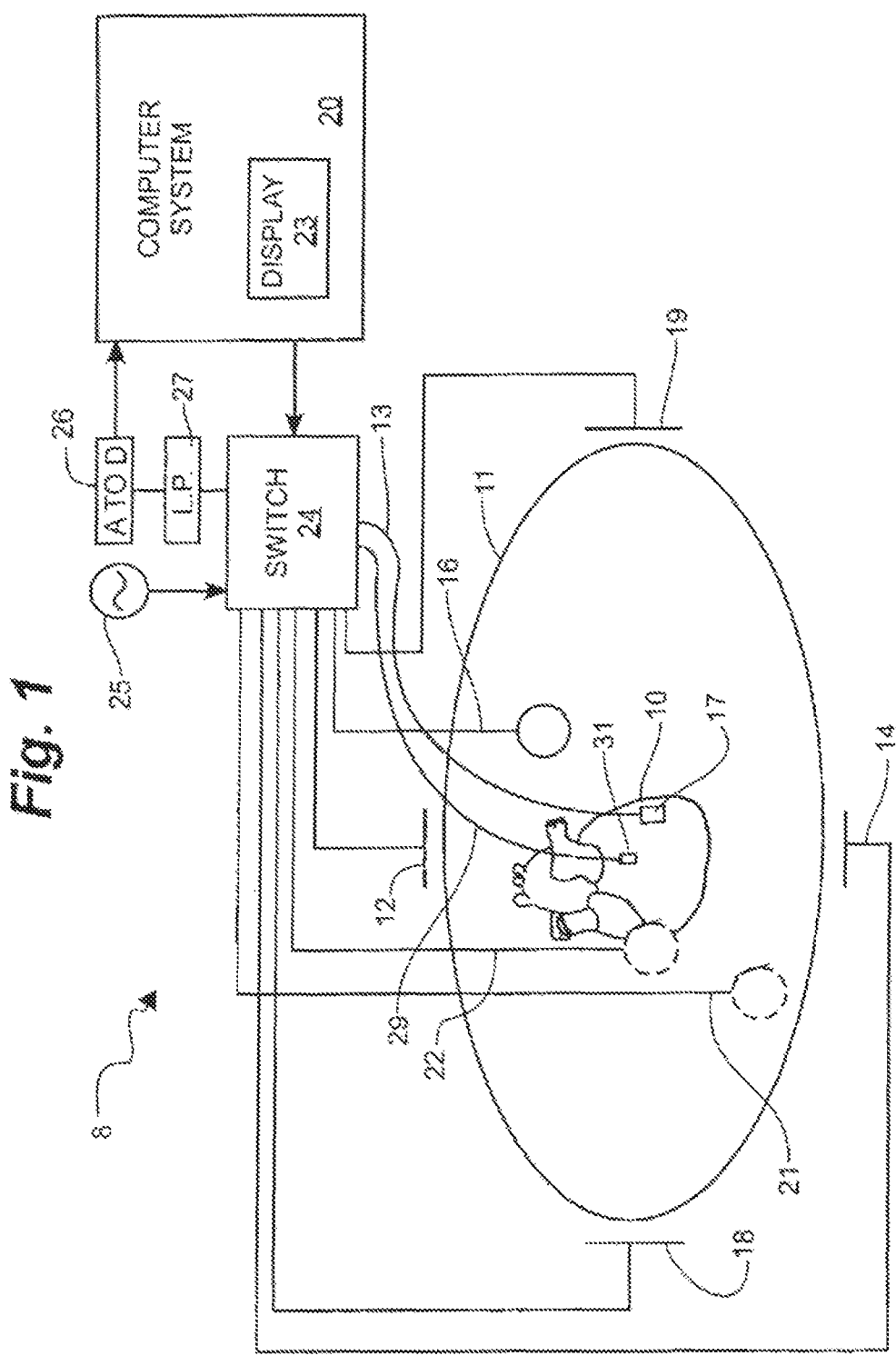
FIG. 1 is a schematic depiction of a localization system utilized in an electrophysiology study.

FIG. 1 shows a schematic diagram of a localization system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface, and store the measured data in association with location information for each measurement point at which the electrophysiology data was measured, for example to create a diagnostic data map of the patient's heart 10. As one of ordinary skill in the art will recognize, and as will be further described below, localization system 8 determines the location of objects, typically within a three-dimensional space, and expresses those locations as position information determined relative to at least one reference.

For simplicity of illustration, the patient 11 is depicted schematically as an oval. Three sets of surface electrodes (e.g., patch electrodes) are shown applied to a surface of the patient 11, defining three generally orthogonal axes, referred to herein as an x-axis, a y-axis, and a z-axis. The x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram (ECG) system leads in place. This ECG information is available to the system 8, although not illustrated in FIG. 1.

A representative catheter 13 having at least one electrode 17 (e.g., a distal electrode) is also shown. This representative catheter electrode 17 is referred to as the "roving electrode," "moving electrode," or "measurement electrode" throughout the specification. Typically, multiple electrodes on catheter 13, or on multiple such catheters, will be used. In one embodiment, for example, localization system 8 may comprise up to sixty-four electrodes on up to twelve catheters disposed within the heart and/or vasculature of the patient. Of course, this embodiment is merely exemplary, and any number of electrodes and catheters may be used within the scope of the present invention.

An optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrode 17, and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to the multiplex switch 24, and the pairs of surface electrodes are selected by software running on a computer 20, which couples the electrodes to a signal generator 25. The computer 20, for example, may comprise a conventional general-purpose computer, a special-purpose computer, a distributed computer, or any other type of computer. The computer 20 may comprise one or more processors, such as a single central processing unit (CPU), or a plurality of processing units, commonly referred to as a parallel processing environment, which may execute instructions to practice the various aspects of the present invention described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternately, these orthogonal fields can be decomposed and any pairs of surface electrodes can be driven as dipoles to provide effective electrode triangulation. Additionally, such non-orthogonal methodologies add to the flexibility of the system. For any desired axis, the potentials measured across an intra-cardiac electrode 17 resulting from a predetermined set of drive (source-sink) configurations are combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The measurement electrode 17 placed in the heart 10 is exposed to the field from a current pulse and is measured with respect to ground, such as belly patch 21. In practice the catheters within the heart may contain multiple electrodes and each electrode potential may be measured. As previously noted, at least one electrode may be fixed to the interior surface of the heart to form a fixed reference electrode 31, which is also measured with respect to ground, such as belly patch 21. Data sets from each of the surface electrodes, the internal electrodes, and the virtual electrodes may all be used to determine the location of the measurement electrode 17 or other electrodes within the heart 10.

The measured voltages may be used to determine the location in three-dimensional space of the electrodes inside the heart, such as the roving electrode 17, relative to a reference location, such as reference electrode 31. That is, the voltages measured at reference electrode 31 may be used to define the origin of a coordinate system, while the voltages measured at roving electrode 17 may be used to express the location of roving electrode 17 relative to the origin. Preferably, the coordinate system is a three-dimensional (x, y, z) Cartesian coordinate system, though the use of other coordinate systems, such as polar, spherical, and cylindrical coordinate systems, is within the scope of the invention.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described in U.S. Patent Application Publication No. 2004/0254437, which is hereby incorporated herein by reference in its entirety. The electrode data may also be used to compensate for changes in the impedance of the body of the patient as described in co-pending U.S. patent application Ser. No. 11/227,580, filed on 15 Sep. 2005, which is also incorporated herein by reference in its entirety.

In summary, the system 8 first selects a set of surface electrodes and then drives them with current pulses. While the current pulses are being delivered, electrical activity, such as the voltages measured at least one of the remaining surface electrodes and in vivo electrodes, is measured and stored. Compensation for artifacts, such as respiration and/or impedance shifting, may be performed as indicated above.

In a preferred embodiment, the localization/mapping system is the EnSite NavX™ navigation and visualization system of St. Jude Medical, Atrial Fibrillation Division, Inc. Other localization systems, however, may be used in connection with the present invention, including for example, the CARTO navigation and location system of Biosense Webster, Inc. The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377

Figure 2:
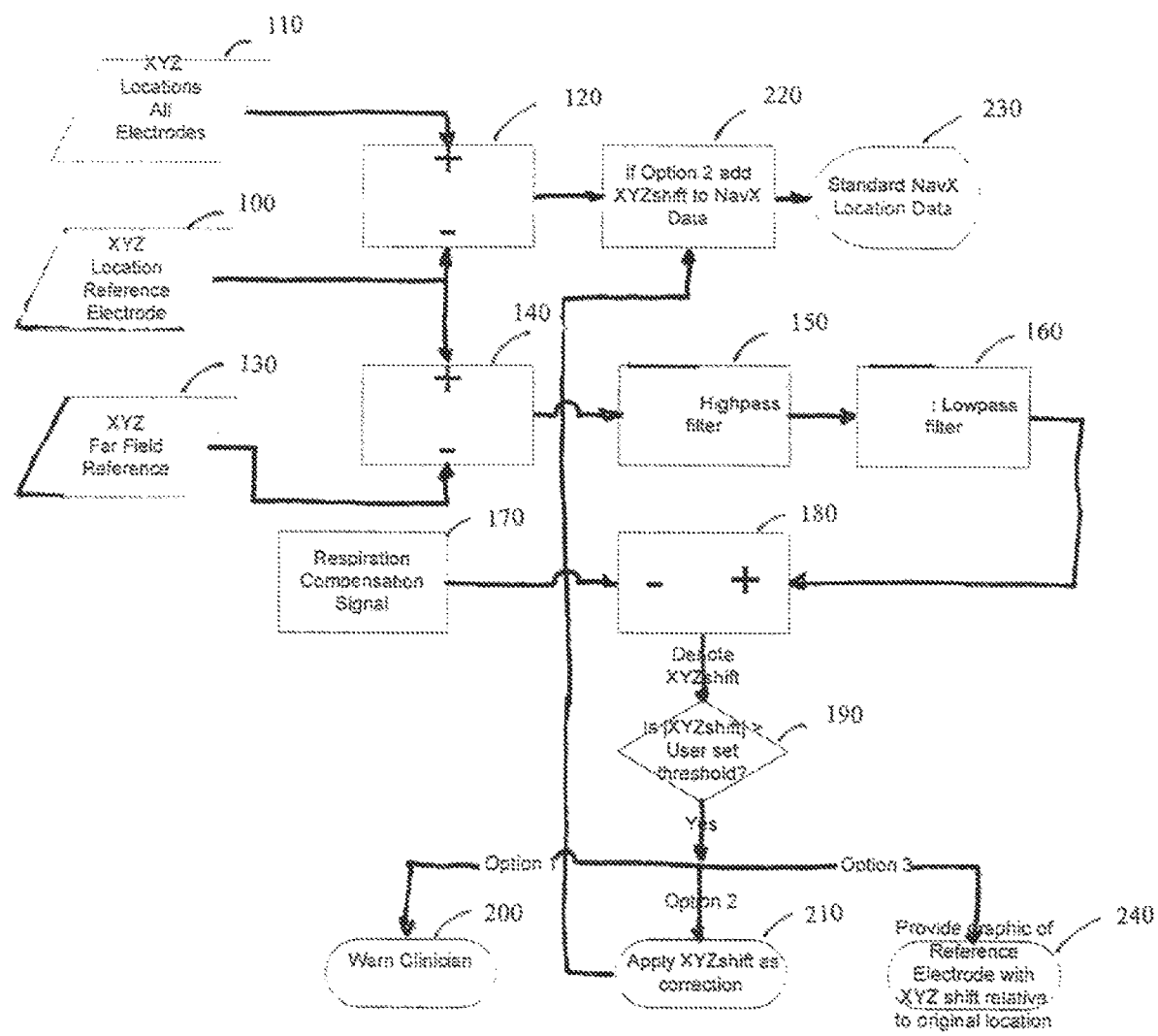
FIG. 2 is a flowchart that illustrates navigational reference dislodgement detection and mitigation functions according to an embodiment of the present invention.

Various aspects and features of the present invention will now be described with reference to FIG. 2. In use, a navigational reference or local reference, such as reference electrode 31, is secured at an initial reference location, preferably internal to the body of patient 11 (block 100). The initial reference location is defined as a reference point (e.g., the origin) of a coordinate system that may be used to locate points in space. As it moves within heart 10, the location of roving electrode 17 (block 110) may be measured relative to the coordinate system having the initial reference location as its origin (block 120), thereby outputting position information that defines the location of roving electrode 17 in the coordinate system that uses the initial reference location as its reference point.

As one of ordinary skill in the art will recognize, and as described above, reference electrode 31 may become dislodged from the initial reference location during the course of an electrophysiology study, for example if the physician inadvertently tugs on the catheter 29 carrying reference electrode 31, effectively moving the origin of the coordinate system relative to which the position of roving electrode 17 is measured and invalidating any positions of roving electrode 17 measured after the dislodgement. It is desirable, therefore, for a controller to monitor for dislodgement of the navigational reference from the initial reference location, and, if such dislodgement occurs, to generate a signal indicative of the dislodgement, for example to alert the user that a dislodgement has occurred.

Thus, the navigational reference may be coupled to a circuit in order to generate an output signal, which may be monitored for an increase above a threshold indicative of the navigational reference having dislodged from the initial reference location. For example, the velocity of the navigational reference may be monitored, and, if the velocity of the navigational reference exceeds a preset threshold, one may conclude that the navigational reference has dislodged from the initial reference location; if the navigational reference remains stationary, its velocity is nominally zero. Similarly, an acceleration vector could be monitored, and again, any change that is above a threshold (near zero) would be indicative of movement. It should be understood that the threshold may also be implemented as a minimum acceptable value rather than a maximum acceptable value, such that dislodgment may be detected unless the monitored output signal is greater than the minimum acceptable value threshold.

In other embodiments of the invention, a far field reference, such as belly patch 21, is provided outside the body of patient 11 (block 130). Of course, the far field reference may be spaced apart from the body. Dislodgment may be detected by monitoring a location of the navigational reference relative to the far field reference (block 140). If the positional relationship between the navigational reference and the far field reference changes beyond a preset threshold, one may conclude that the navigational reference has become dislodged from the initial reference location. This may be accomplished, for example, by coupling both the navigational reference and the far field reference to a circuit in order to generate an output signal, which may be monitored for a signal that is indicative of the navigational reference having dislodged from the initial reference location.

Preferably, the output signal generated above is a displacement vector of the navigational reference relative to the far field reference. Typically, where the navigational reference has not become dislodged from the initial reference location, the displacement vector will be nominally 0 (that is, approximately [0, 0, 0]). However, as one of ordinary skill in the art will recognize, there are error sources inherent in localization system 8, especially across distances that typically exist between the navigational reference and the far field reference, and it is desirable to account for these error sources. One such error source is DC or very low frequency drift. Accordingly, the output signal may be filtered with a high pass filter (block 150) having a cutoff frequency of about 0.01 Hz, and more preferably about 0.001 Hz. Additional error sources are respiration, patient movement, and cardiac motion (e.g., the beating of the heart 10), which tend to produce variations having frequency components of a fraction of 1 Hz in the case of respiration, to greater than 1 Hz with harmonics ranging to several Hz for cardiac motion. Accordingly, it may be desirable to also filter the output signal with a low pass filter (block 160) having a cutoff frequency of about 0.1 Hz to about 0.5 Hz, and more preferable about 0.15 Hz, and it may be desirable to include a respiration compensation value as described above (block 170). The filtered output signal (block 180) may be monitored for a signal that is indicative of the navigational reference having dislodged from the reference location. As described above, it is desirable that the filtered output signal be a displacement vector that is approximately 0; thus, the filtered output signal may be monitored for a signal with an absolute amplitude that is above a dislodgement threshold (block 190). If such a signal is detected, the user (e.g., a physician or clinician) may be warned (block 200), for example with an audible alarm, a visual cue, or a both an audible alarm and a visual cue.

In addition to providing automatic dislodgement detection, the present invention also provides dislodgement mitigation or correction. Typically, dislodgement mitigation involves the user (e.g., a physician) repositioning the navigational reference to the initial reference location, thereby re-establishing the original coordinate system. In some embodiments of the invention, it is indeed contemplated that the user may be provided with guidance, such as positional feedback of the navigational reference or a graphic depiction of the dislodged location of the navigational reference relative to the initial reference location (block 240), to assist the user in repositioning and securing the navigational reference to the initial reference location. It is also contemplated that, upon detecting a dislodgement, a computer may be utilized to control a servo mechanism, such as that disclosed in U.S. application Ser. No. 11/647,300, filed 29 Dec. 2006 and entitled "Robotic Surgical System", which is hereby incorporated by reference as though fully set forth herein, to reposition and secure the navigational reference to the initial reference location.

Occasionally, however, the navigational reference will reestablish itself in a new, stable position after dislodgement from the initial reference location. If this occurs, it is not necessary to reposition and secure the navigational reference to the initial reference location. Rather, the new, dislodged (or post-dislodgement) location of the navigational reference may be used to define the origin of a new coordinate system. Thus, after determining the post-dislodgement location of the navigational reference, a reference adjustment (e.g., a coordinate transformation) may be calculated that relates the original coordinate system (that is, the coordinate system having an origin at the initial reference location) to the new coordinate system (that is, the coordinate system having an origin at the post-dislodgement location), thereby compensating for the movement of the navigational reference from the initial reference location to the dislodged location (block 210). The location of roving electrode 17 may be measured relative to the new coordinate system, and, by applying the reference adjustment (block 220), the location of roving electrode 17 may be defined relative to the original coordinate system such that all location information data for roving electrode 17 may be expressed relative to the original coordinate system having the initial reference location as its reference point (block 230).

It is contemplated that roving electrode 17 may also be utilized to measure electrophysiology information on the surface of heart 10, including, without limitation, voltages, impedances, and complex fractionated electrogram (CFE) information, such as discussed in U.S. application Ser. No. 11/647,276, filed 29 Dec. 2006 and entitled "System and Method for Mapping Electrophysiology Information Onto Complex Geometry", which is hereby incorporated by reference as though fully set forth herein. Electrophysiology information may also be measured by the navigational reference, such as reference electrode 31. Since reference electrode 31 and roving electrode 17 are proximate each other, they will experience common noise signals, such as those generated by patient motion, respiration, and cardiac motion. Advantageously, by simultaneously measuring electrophysiology information at both roving electrode 17 and reference electrode 31, the output of roving electrode 17 may be adjusted by compensating for at least one signal that is common to both roving electrode 17 and reference electrode 31, for example by subtracting the output from reference electrode 31 from the output from roving electrode 17 according to the principle of common mode rejection.

Although several embodiments of this invention have been described above with a certain degree of particularity, those skilled in the art could make numerous alterations to the disclosed embodiments without departing from the spirit or scope of this invention. For example, though electrode 31 has been described as the initial reference location, one of ordinary skill in the art will recognize that all suitable navigational references, including, without limitation, magnetic coil sensors, may be utilized instead of or in addition to electrode 31 without departing from the spirit and scope of the present invention. Further, though belly patch 21 has been described as the far field reference, one of ordinary skill in the art will recognize that any suitable reference located outside the patient's body at an external reference location may be utilized as the far field reference.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of tracking a position of a catheter with a localization system, comprising:
    defining an initial reference location of a navigational reference as a reference point for a coordinate system for locating positions of points in space;
    monitoring a velocity of the navigational reference for an indication of a dislodgement of the navigational reference from the initial reference location; and
    generating a signal indicating that the navigational reference has dislodged from the initial reference location when the velocity of the navigational reference exceeds a preset dislodgement threshold.

2. The method according to claim 1, further comprising providing guidance to a user to help re-position and secure the navigational reference to the initial reference location.

3. The method according to claim 1, further comprising:
    determining a post-dislodgement location of the navigational reference after it has dislodged from the initial reference location;
    calculating a reference adjustment to compensate for the navigational reference having changed positions from the initial reference location to the post-dislodgement location of the navigational reference.

4. The method according to claim 3, further comprising using the reference adjustment to generate location information data for a moving electrode, the location information data comprising position information that defines the location of the moving electrode with reference to a coordinate system that uses the initial reference location as its reference point.

5. The method according to claim 1, further comprising:
    providing a far field reference;
    wherein the monitoring step comprises monitoring a rate of change in a location of the navigational reference relative to the far field reference and generating a signal indicating dislodgement when the rate of change in the location of the navigational reference relative to the far field reference exceeds a preset threshold.

6. The method according to claim 1, further comprising:
    simultaneously measuring a first electrophysiological signal using a moving electrode and a second electrophysiological signal using the navigational reference;
    adjusting an output of the first electrophysiological signal by compensating for at least one signal component that is common to each of the first electrophysiological signal and the second electrophysiological signal.

7. The method according to claim 1, wherein the monitoring step comprises:
    coupling the navigational reference to a circuit to generate an output signal; and
    monitoring the output signal for an increase above a threshold indicative of the navigational reference having dislodged from the initial reference location.

* * * * *